United States Patent [19]

Shinozaki et al.

[11] Patent Number: 5,034,324
[45] Date of Patent: Jul. 23, 1991

[54] MICROORGANISM IMMOBILIZED IN A GEL PREPARED FROM POLYVINYL ALCOHOL AND A POLYSACCHARIDE

[75] Inventors: Atushi Shinozaki, Okayama; Kunio Abe, Kurashiki, both of Japan

[73] Assignee: Kuraray Company, Ltd., Kurashiki, Japan

[21] Appl. No.: 224,356

[22] Filed: Jul. 26, 1988

[30] Foreign Application Priority Data

Aug. 10, 1987 [JP] Japan ............................... 62-200599

[51] Int. Cl.⁵ ........................ C12N 11/10; C12N 11/04
[52] U.S. Cl. ..................................... 435/178; 435/182
[58] Field of Search ............... 435/177, 178, 180, 182; 264/4, 28

[56] References Cited
U.S. PATENT DOCUMENTS 4,138,292 2/1979 Chibata et al. ...................... 435/178
4,617,271 10/1986 Nambu ................................ 435/182

Primary Examiner—David M. Naff
Attorney, Agent, or Firm—Oblon, Spivak, McClelland, Maier & Neustadt

[57] ABSTRACT

A hydrated gel of high water content and high porosity containing an immobilized microorganism is prepared by dropwise addition of an aqueous solution containing a microorganism, polyvinyl alcohol and a polysaccharide to an aqueous solution containing polyvalent metal ions to gel the polysaccharide and form spherical gel beads, and subjecting the beads to at least one cycle of freezing and thawing to gel the polyvinyl alcohol. The polysaccharide can be sodium alginate and the polyvalent metal ions can be provided by calcium chloride. Freezing is at a temperature not higher than −5° C., and the cycle of freezing and thawing is preferably repeated at least two times.

8 Claims, 3 Drawing Sheets

MICROORGANISM IMMOBILIZED IN A GEL PREPARED FROM POLYVINYL ALCOHOL AND A POLYSACCHARIDE

BACKGROUND OF THE INVENTION

1. Field of the Invention

This invention relates to a process for manufacturing high-strength, spherical hydrated gel containing microorganism immobilized therein.

2. Description of the Prior Art

Studies have been under way on immobilization of enzymes or microorganisms to efficiently utilize their functions as biocatalysts, and some of the results have been put to practical use.

As a method of immobilizing enzymes or microorganisms is known the entrapped immobilization technique, in which enzymes or microorganisms are retained inside a polymeric material. The polymers frequently used for this purpose include agar, salts of alginic acid, K-carrageenan, polyacrylamide, polyvinyl alcohol and photo-curable polymers. Of these, polyvinyl alcohol (hereinafter abbreviated as PVA in some cases) can be converted into gel of high water content having excellent water resistance, elasticity and flexibility if its aqueous solution is frozen at a temperature not higher than $-5°$ C., followed by thawing at ordinary temperature, and this freeze-thaw gel can be used as a desirable carrier for immobilizing enzymes and microorganisms [Japanese Patent Kokoku No. 47-12854 (1972)]. It is also known that this PVA gel shows sufficiently high mechanical strength not to be expected with other polymers, if the freeze-thaw operation is repeated or if the freezing operation is followed by vacuum dehydration [Japanese Patent Kokai No. 58-47492 (1983)].

The polymeric materials used for immobilizing microorganisms must be nontoxic and have no adverse effect upon microorganisms. In this respect, freeze-thaw PVA gel shows high safety to living bodies because no chemical agent is used for gel formation. In addition, its high water content and porous structure make it ideal for use as a carrier suitable for the culture and propagation of the microorganisms immobilized therein.

Reactors in which bioreactions are carried out in the presence of an enzyme or microorganism immobilized by this entrapped method are various in type: fixed bed (packed column), fluidized bed, and stirrer-equipped tank. The shape of carrier used in these reactors should preferably be spherical in terms of large active area, high fluidity and packing efficiency, and ease of handling.

For commercial production, it is important that high-strength, spherical carriers be manufactured by simple operations and at a low cost.

Salts of alginic acid, which have also been used extensively as a low-cost and easy-to-handle carrier for immobilizing enzymes or microorganisms, readily form spherical gel beads when an aqueous solution of sodium alginate is added dropwise at ordinary temperature to an aqueous solution containing polyvalent metal ions, such as $Ca^{2+}$ and $Al^{3+}$. However, gel beads of this type are damaged by a salt of phosphoric acid, and tend to be eroded or dissolved when used for waste water treatment. In addition, these are liable to destruction when used over long periods in a reactor because of the insufficient mechanical strength.

Gels formed from photo-curable resins and polyacrylamide can also be shaped into spheres at ordinary temperature, but their practical application as carrier for entrapped immobilization is limited only to bioreactions which yield products of high added value [Japanese Patent Kokai No. 61-216688 (1986)] because of the far higher material cost compared with PVA gel.

PVA gel by freeze-thaw method may preferably be molded into spheres when used as carrier for immobilizing microorganisms. However, no suitable method has yet been established to mass-produce by simple operations spherical PVA gel beads with a diameter in the range from 1 to 10 mm—a shape most preferred for the purpose.

Various methods are known for molding PVA gel into spheres: putting an aqueous solution of PVA in a spherical mold and subjecting to freeze-thaw treatment [Japanese Patent Kokai No. 58-47492 (1983)]; adding an aqueous solution of PVA dropwise to a recessed, hemispherical mold immersed in a liquid, such as oil and organic solvents, and subjecting the whole system to freeze-thaw treatment [Japanese Patent Kokoku No. 54-1501 (1979)]; adding an aqueous solution of PVA to a dispersant, such as oil and organic solvents, with stirring, thereby forming microspheres of PVA gel with a diameter in the range from 0.1 $\mu$m to 1 mm [Japanese Patent Kokai No. 62-45637 (1987)]; and adding an aqueous solution of PVA containing enzymes or microorganisms dropwise to saturated solution of boric acid to form spheres of PVA gel containing enzymes or microorganisms [Japanese Patent Kokai No. 61-100193 (1986)], and furthermore followed by freeze-thaw treatment [Japanese Patent Kokai No. 61-139385 (1986)].

In addition, Japanese Patent Kokai No. 62-138193 (1987) discloses "a process for manufacturing granular moldings containing enzymes or microbial cells immobilized therein, which comprises dropwise addition of an aqueous composition containing (A) polyvinyl alcohol, (B) a water-soluble polysaccharide capable of gelation upon contact with at least one member of polyvalent metal ions and (C) an enzyme or microbial cells to an aqueous medium containing polyvalent metal ions and boric acid, thereby gelling said aqueous composition into granules."

The above-mentioned methods using molds require the same number of molds as that of spherical moldings to be manufactured and freezing devices, and hence are not desirable for continuous production of spherical PVA gel in large quantities in terms of installation and freezing costs.

On the other hand, the methods using organic solvents, oil and chemical agent such as boric acid, are also undesirable and have limited use because of possible adverse effects of these chemicals upon microorganisms and possible contamination of PVA gel with impurities.

SUMMARY OF THE INVENTION

The object of this invention is to provide a low-cost process for mass-producing high-strength, spherical hydrated gel for immobilizing microorganisms without using any mold, which requires high installation and running costs, nor any chemical agent, which can adversely affect microorganisms, by utilizing the outstanding characteristics of hydrated PVA gel by freege-thaw method (high water content and high porosity).

PVA gel of this invention has desirable characteristics as a carrier for entrapped immobilization of microorganisms: high affinity for microorganisms, mechanical strength and durability sufficiently high for use in any type of reactor; and high resistance to water and chemicals. This invention provides a technique to mold this PVA gel into spheres by a simple operation of freezing without using any chemical agent harmful to microorganisms.

Figure 1:
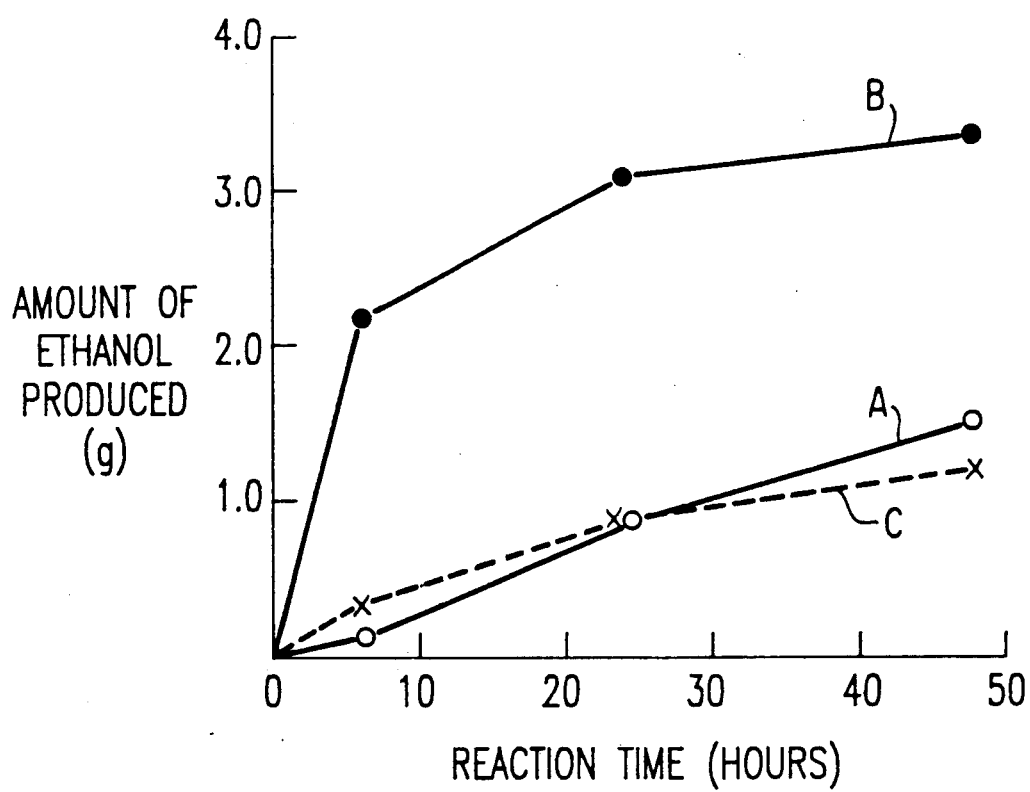
In FIG. 1, kinked line A represents the amount (in grams) of ethanol formed when an yeast immobilized in PVA gel is directly submitted to bioreaction; kinked line B shows the amount (in grams) of ethanol formed when the immobilized yeast is cultured and propagated inside the gel and then submitted to bioreaction; and kinked line C represents the amount (in grams) of ethanol formed when the yeast not immobilized is subjected to bioreaction (Reference Example).

Line G represents the denitrifying activity of microbial cell immobilized in PVA gel obtained by the use of boric acid (Comparative Example 1).

DETAILED DESCRIPTION OF THE PREFERRED EMBODIMENTS

Under the circumstances as described above, we investigated the effects of salts of alginic acid (an acidic polysaccharide extracted from sea weeds, which was known to readily form spherical gel particles upon contact with polyvalent metal ions, such as $Ca^{2+}$ and $Al^{+3}$, and was extensively used as carrier for entrapped immobilization of microbial cells) and the like on PVA gel formation. As a result, it was discovered that if an aqueous solution containing (A) a microorganism, (B) polyvinyl alcohol, and (C)-① a water-soluble polysaccharide capable of gelation upon contact with at least one member of polyvalent metal ions, or (C)-② a compound which produces polyvalent metal ions in aqueous medium (hereinafter abbreviated as a compound having polyvalent metal ions), is added dropwise to an aqueous solution of a compound having polyvalent metal ions when said solution of mixed compounds contains a water-soluble polysaccharide capable of gelation upon contact with at least one member of polyvalent metal ions [(C)-①], or to an aqueous solution of a water-soluble polysaccharide capable of gelation upon contact with at least one member of polyvalent metal ions when said solution of mixed compounds contains a compound having polyvalent metal ions [(C)-②], spherical gel beads are readily formed, which do not stick to one another under moderate agitation because their surfaces have been rapidly solidified, thus giving spherical moldings of immobilized microorganism having mechanical strength sufficiently high to withstand succeeding treatments.

As stated above, the process of this invention includes the following two patterns:

[I] a method in which an aqueous solution containing (A) a microorganism, (B) polyvinyl alcohol, and (C)-① a water-soluble polysaccharide capable of gelation upon contact with at least one member of polyvalent metal ions is added dropwise to an aqueous solution of a compound having polyvalent metal ions, and the spherical moldings thus formed are then subjected to at least one cycle of freezing (at a temperature not higher than $-5°$ C.) and thawing, thereby perfecting the gelation of polyvinyl alcohol, and [II] a method in which an aqueous solution containing (A) a microorganism, (B) polyvinyl alcohol, and (C)-② a compound having polyvalent metal ions is added dropwise to an aqueous solution of a water-soluble polysaccharide capable of gelation upon contact with at least one member of polyvalent metal ions, and the spherical moldings thus formed are then subjected to at least one cycle of freezing (at a temperature not higher than $-5°$ C.) and thawing, thereby perfecting the gelation of polyvinyl alcohol.

Of these, the former method [I] is better than the latter [II] in terms of ease of handling, operability and other points. Hence, this invention will be explained below in more detail, with the method [I] being taken as example.

As the water-soluble polysaccharide capable of gelation upon contact with at least one member of polyvalent metal ions [compound (C)-①] and as the compound having polyvalent metal ions [compound (C)-②], will be taken in the following explanations sodium alginate and calcium chloride ($CaCl_2$), respectively, as the most preferred example.

That the spherical moldings formed from the PVA solution do not stick to one another in the $CaCl_2$ solution and retain a certain level of mechanical strength greatly benefits the ease of handling and the compactness of equipment in mass-production of freeze-thaw PVA gel on a continuous basis.

The spherical moldings separated from the $CaCl_2$ solution are then subjected to at least one cycle of freezing (at a temperature not higher than $-5°$ C.), maintaining at that temperature for at least two hours and thawing (at a temperature that will not affect the microorganism involved), thus giving spherical hydrated PVA-gel containing the microorganism immobilized therein.

The mechanical strength of the PVA gel can be markedly enhanced by repeating the above-mentioned cycle of freeze-thaw treatment two times or more.

In the process of this invention, sodium alginate not only serves as an molding aid for the aqueous PVA solution, but also helps enhance the gel strength and eliminate the surface stickiness of gel beads. This allows simpler freeze-thaw conditions (such as freezing temperature, freezing time, and the number of freeze-thaw cycles), thus greatly shortening the time required for preparation for immobilization of microorganisms by PVA gel).

The PVA gel beads thus prepared still retain the outstanding characteristics of freeze-thaw PVA gel suitable for immobilization and propagation of microorganisms, are spherical in shape, have high mechanical strength, and can be manufactured more easily and at lower costs compared with conventional methods for producing spherical PVA gel. Hereinafter, the process of this invention will be explained in more detail.

PVA used in the process of this invention should preferably has an average polymerization degree of 1000 or higher, most preferably 1700 or higher, and a saponification degree of 98.5 mol % or higher, most preferably 99.85 mol % or higher (completely saponified PVA), in order to ensure efficient gel formation. The degree of saponification, in particular, is a critical factor; PVA of a lower saponification degree requires more severe freezing conditions (lower freezing temperature and longer freezing time) to achieve an expected level of mechanical strength. This is unfavorable in terms of productivity.

In the process of this invention, may also be used any known modified PVA so long as it does not defeat the intended purpose of this invention.

The concentration of aqueous PVA solution used in the process of this invention may be at a level capable of gel formation, ranging from 3 to 40 weight %. Within this range, the higher the PVA concentration, the higher the mechanical strength of formed gel. However, a lower PVA concentration is more preferable in terms of material cost, so long as a necessary level of mechanical strength can be achieved. The proper PVA concentration should be determined with considerations given also to the kinds and amounts of other components in the system, the solution temperature and the type of dropping device used. When the PVA solution is added dropwise at ordinary temperature, a PVA concentration in the range from 5 to 10 weight % readily forms spherical gel beads with mechanical strength sufficiently high for practical use.

As examples of the water-soluble polysaccharide capable of gel formation upon contact with at least one member of polyvalent metal ions [(C)-①], there may be mentioned alkali metal salts of alginic acid, carrageenan, mannan and chitosan. Of these, sodium alginate is the most preferred.

As the compound having polyvalent metal ions [(C)-②], may be mentioned those compounds which contain at least one member of polyvalent metal ions selected from ions of alkaline earth metals (e.g., magnesium, calcium, strontium and barium), aluminum ions, cerium ions and nickel ions. Of these, $CaCl_2$ is the most preferred.

The combination of sodium alginate anc $CaCl_2$ is the most preferred in the process of this invention.

The concentration of water-soluble polysaccharide to be added to the aqueous solution of PVA [(C)-①; preferably sodium alginate] should preferably be 0.2 to 4 wt % based on the weight of water, most preferably 0.5 to 2 weight %. If the concentration is less than 0.2 weight %, the resulting aqueous solution is poor in the capability of forming spherical gel beads. A concentration higher than 4 weight %, on the other hand, gives rigid spherical beads, but leads to an increase in solution viscosity and can add to the material cost.

To an aqueous solution of PVA and sodium alginate thus prepared, is then added with stirring an aqueous suspension of microbial cells to be immobilized.

Any type of microorganisms can be used in the process of this invention. Illustrative examples include molds belonging to the genera *Aspergillus* and *Rhizopus*, bacteria belonging to the genera *Pseudomonas, Acetobacter, Streptomyces, Escherichia* and *Alcarigenes*, and yeasts belonging to the genera *Saccharomyces* and *Candida*.

The PVA solution containing microbial cells thus obtained may also include a culture medium for the microorganism, a reinforcing material for enhancing the mechanical strength of immobilization carrier, a filler to regulate the specific gravity of formed gel, a protective agent for the microorganism against possible damages caused by freezing, and other additives, in a amounts that will not affect the gelation of PVA.

The PVA solution obtained above was then charged, for example, in syringe and added dropwise to an aqueous solution of compound having polyvalent metal ions (preferably $CaCl_2$) through a tubular orifice like a syringe needle.

The concentration of $CaCl_2$ solution should preferably be in the range from 0.05 to 1.0 mol/l, most preferably in the range from 0.1 to 0.5 mol/l, to ensure sufficient mechanical strength of formed gel beads.

The droplets released from the orifice, upon contact with the aqueous solution of $CaCl_2$, take a spherical shape by the action of surface tension, and the outermost surface of each sphere rapidly solidifies to form a thin-film layer, thus giving spherical moldings. The diameter of these spherical moldings can be freely adjusted within the range from 1 to 10 mm by properly setting the diameter of orifice and the viscosity of PVA solution. The aqueous solution of $CaCl_2$ may be kept still, but forced agitation of the $CaCl_2$ solution by means of a stirrer or the like will accelerate the reaction between the moldings of PVA solution and $CaCl_2$ solution, thereby perventing the spherical moldings from sticking to one another almost completely. In commercial mass-production of spherical moldings, the aqueous solution of $CaCl_2$ may be ejected by means of a pump or the like to achieve spherical moldings of uniform diameter. For example, use of a roller pump, which is designed to supply an intermittent flow of liquid by pressing a flexible tube, will eject droplets of a constant volume from the orifice, thus favoring the formation of spherical moldings with a uniform diameter.

The spherical moldings formed in the aqueous solution of $CaCl_2$ are separated from the solution and then subjected to freezing operation. The freezing temperature should be $-5°$ C. or lower, more preferably $-20°$ C. or lower, to obtain PVA gel beads of higher mechanical strength. The freezing time is two hours of longer, more preferably ten hours or longer. This freezing operation is to perfect the gelation of PVA, and the frozen gel is then allowed to stand at a temperature that will not affect the microorganism involved (thawing), affording final spherical hydrated PVA gel.

These spherical PVA gel beads of this invention can be obtained after one cycle of freeze-thaw treatment. Sometimes it may be insufficient in mechanical strength in some cases depending on the composition of PVA solution and the freezing conditions adopted. Hence, the freeze-thaw operation should preferably be repeated at least two times, most preferably at least three times, to ensure sufficiently high mechanical strength of spherical hydrated gel.

The freeze-thaw PVA gel thus obtained can be used in any type of reactor with no danger of deformation, destruction, or attack by water or various chemicals, thus allowing continuous operation over long periods, and is therefore ideal for practical use as moldings of immobilized microorganism.

In the process of this invention, the water-soluble polysaccharide added to the aqueous PVA solution [(C)-①; preferably sodium alginate] not only serves as a molding aid for PVA, but also exhibits the unexpected effect that it helps enhance the mechanical strength of final gel beads after freeze-thaw treatment compared with the PVA gel without sodium alginate. In addition, it also shows a unique effect to minimize the surface stickiness of gel beads.

The reason why such outstanding effects are achieved is not absolutely clear yet. It may be assumed that such results stem from a synergistic effect of the three components: PVA, the water-soluble polysaccharide capable of gelation upon contact with at least one member of polyvalent metal ions, and the compound having polyvalent metal ions.

As is apparent from the foregoing, this invention provides a process for manufacturing high-strength, spherical moldings of immobilized microorganism made of hydrated PVA gel by simple operations and at a low cost without using any chemical agent harmful to microorganisms, and is expected to promote widespread application of bioreactions using microorganisms.

The following Examples will further illustrate the invention.

EXAMPLE 1

Polyvinyl alcohol (PVA) (average polymerization degree: 1740, saponification degree: 99.85 mol %; product of KURARAY CO., LTD.) was washed with hot water of 40° C. for about one hour, them mixed with water in an amount so as to give a total weight of 40 g and a final PVA concentration of 8 weight %, and the pH was adjusted to 6. This mixture was heated at 120° C. for 30 minutes in an autoclave, and the resulting PVA solution was allowed to cool to room temperature. It was mixed with 0.4 g sodium alginate, 4 ml of a sterile water containing 0.5 g-wet cells/ml of *Saccharomyces cereviciae*, and the mixture was stirred well.

The solution thus obtained was run at a rate of 1 ml/min by means of a roller pump equipped with a vinyl tubing 2 mm in internal diameter having a syringe needle of 0.8 mm internal diameter at the tip of it, and added dropwise with stirring to a 0.5 mol/l aqueous solution of $CaCl_2$ from a height of 5 cm above the surface level. The released droplets at once sedimented in the aqueous solution of $CaCl_2$ in the form of spheres. These spherical particles were all separated from the $CaCl_2$ solution, carefully washed with sterile water, and frozen at $-27° \pm 3°$ C. in a refrigerator for 20 hours. Thawing at room temperature gave opaque, yellowish-white, flexible, spherical gel beads with no surface stickiness. The above freeze-thaw treatment was further repeated two times to enhance the gel strength.

The total weight of the thus obtained spherical PVA gel containing the yeast immobilized therein was 32 g (with part of the product being left attached to the containers, etc. during the manufacturing process). The average diameter of the spherical PVA gel was 3.6 mm. The total number amounted to about 1200, and the water content was 89 wt %.

The gel beads obtained above were divided into two equal parts, one part was added to 100 g of a solution for producing ethanol (containing 10 wt % glucose and 60 ppm $MgSO_4.7H_2O$; pH: 6) placed in a 500-ml conical flask, and the mixture was shaken at 30° C.

The other part was added to 100 ml of an aqueous medium for culture and propagation (containing 1% peptone, 1% yeast extract, 1% glucose and 0.5% sodium chloride; pH: 6) placed in a 500-ml conical flask, the mixture was shaken at 30° C. for 18 hours and then transferred to 100 g of an ethanol producing solution of the same composition as above, and shaking was further continued at 30° C.

Separately, 2 mol of a sterile water containing 0.5 g-wet cells/ml of *Saccharomyces cereviciae* was added to 100 g of an ethanol-preparing solution of the same composition as above, and the mixture was shaken at 30° C. (reaction with free yeast).

A sample was taken from each of the reaction mixtures thus obtained, and analyzed by gas chromatography for the concentration of ethanol formed. The results are summarized in FIG. 1. As can be seen from the figure, the yeast immobilized in PVA gel (curve A) shows activity nearly equal to, or higher than, that of free yeast (curve C). It was also demonstrated that more than two times higher activity can be achieved if the immobilized yeast is cultured and propagated in PVA gel (curve B).

EXAMPLE 2

To determine the effect of sodium alginate added to PVA, specimens were prepared and tested as described below.

PVA (average polymerization degree: 1740, saponification degree: 99.85 mol %; product of KURARAY CO., LTD.) was washed with hot water of 40° C. for about one hour, and heated at 120° C. for 30 minutes in an autoclave, thus preparing the following two types of aqueous PVA solutions, D and E: (D) 10 wt % aqueous solution of PVA (Comparative Example), (E) 10 Wt % aqueous solution of PVA with sodium alginate added thereto in an amount of 1 wt % based on the weight of water. (a case of the present invention)

Each of the two solution, D and E, was poured into a tray (60 mm wide and 95 mm long) to a depth of 10 mm, frozen at $-27° \pm 3°$ C. for 20 hours, and thawed at room temperature, thus affording pieces of hydrated PVA gel 60 mm $\times$ 95 mm $\times$ 10 mm in size.

Solution D gave transluscent, turbid gel with sticky surface (incomplete gelation), while solution E gave opaque turbid gel having a surface with no stickiness (complete gelation).

Figure 2:
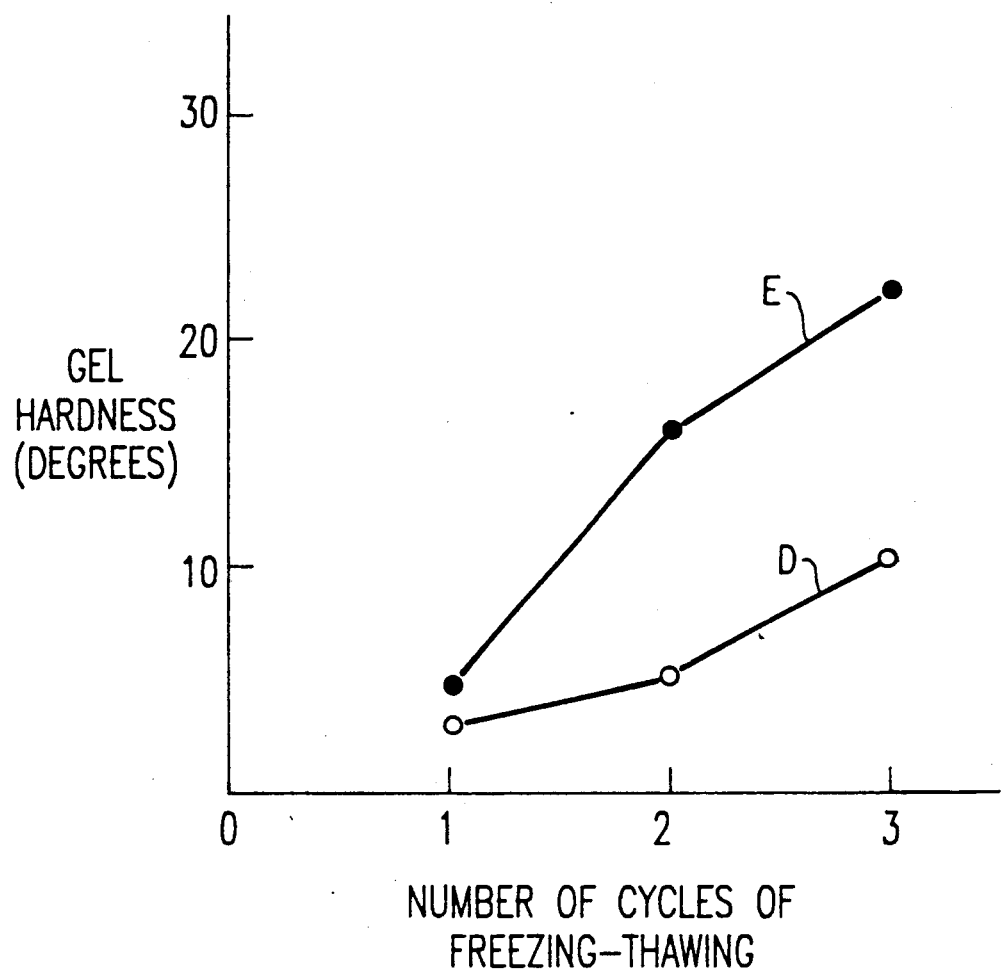
In FIG. 2, kinked line D represents the hardness (in degrees) of gel obtained by subjecting an aqueous solution containing 10 wt % PVA alone to freeze-thaw treatment at a given temperature plotted against the number of freeze-thaw operation cycles (Comparative Example), while kinked line E shows the hardness (in degrees) of gel obtained by subjecting 10 wt % aqueous solution of PVA with sodium alginate added thereto in an amount of 1 wt % based on the weight of water to freeze-thaw treatment at a given temperature plotted against the number of freeze-thaw operation cycles (a case of this invention).

Both of the two specimens D, E obtained above were further subjected to freeze-thaw treatment two times, and the gel hardness was measured after each cycle of thaw-treatment according to the hardness testing procedure specified in JIS K-6301 using Type $C_2$ Rubber Hardness Tester (Kobunshikeiki Co., Ltd.). The results are shown in FIG. 2.

It is apparent from the figure that addition of sodium alginate accelerates the gelation of PVA and greatly enhances the hardness (mechanical strength) of formed gel.

EXAMPLE 3 AND COMPARATIVE EXAMPLE 1

A test was conducted to demonstrate the difference between PVA gel of this invention and PVA gel obtained by the use of boric acid in the performances as carrier for immobilizing microorganisms, particularly in terms of the activity of microorganisms immobilized therein.

The microorganism used in this test is a strain belonging to the genus Pseudomonas. The microbial cell was cultured in Luria's liquid medium with 3% $KNO_3$ added thereto, and the culture solution thus obtained was submitted to immobilization treatment as described below.

(1) Immobilization in hydrated PVA gel by freeze-thaw method of this invention.

An aqueous solution (100 g) containing 8.5 wt % of PVA (completely saponified product with a polymerization degree of 1750, product of KURARAY CO., LTD.), 1 wt % of sodium alginate and 2.0 wt % of ethylene glycol was mixed well by stirring with 10 g of the culture solution prepared above, and this mixture was added dropwise to a 0.2 Mol/l aqueous solution of calcium chloride through a syringe needle. The resulting mixture was stirred for about three minutes, giving spherical PVA gel beads about 3 to 5 mm in diameter. These beads were frozen at $-20°$ C. for about 24 hours and then thawed, and this cycle of operations was repeated two more times (Total: three times), affording gel beads of sufficiently high mechanical strength.

(2) Immobilization in PVA gel obtained by the use of boric acid

An aqueous solution (100 g) containing 8.5 wt % of PVA (completely saponified product with a polymerization degree of 1750, product of KURARAY CO., LTD.) was mixed well by stirring with 10 g of the culture solution prepared above, and the mixture was added dropwise at room temperature to a saturated aqueous solution of boric acid through a syringe needle. The resulting mixture was stirred for about 24 hours, giving spherical PVA gel beads about 3 to 5 mm in diameter.

The two types of PVA gel beads containing immobilized microorganism obtained above were subjected to a comparative test for microbial activity. Each of the gel samples was cultured at 30° C. for 18 hours in a medium of the same composition as used above (Luria's liquid medium with 3% $KNO_3$ added thereto), and then tested for denitrifying activity according to the procedure given below.

Measurement of Denitrifying Activity:

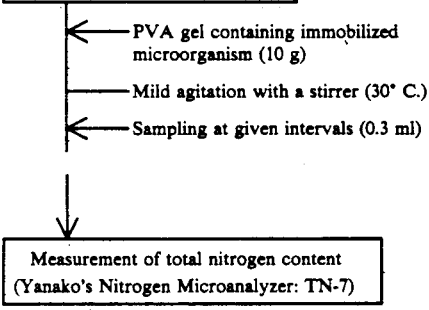

| 0.1M $KNO_2$ or $KNO_3$ | 5 ml |
| 0.1M $CH_3COONa.3H_2O$ | 5 ml |
| 0.5M Phosphate buffer | 20 ml |
| Distilled water | 70 ml |

← PVA gel containing immobilized microorganism (10 g)

— Mild agitation with a stirrer (30° C.)

← Sampling at given intervals (0.3 ml)

↓

Measurement of total nitrogen content (Yanako's Nitrogen Microanalyzer: TN-7)

Figure 3:
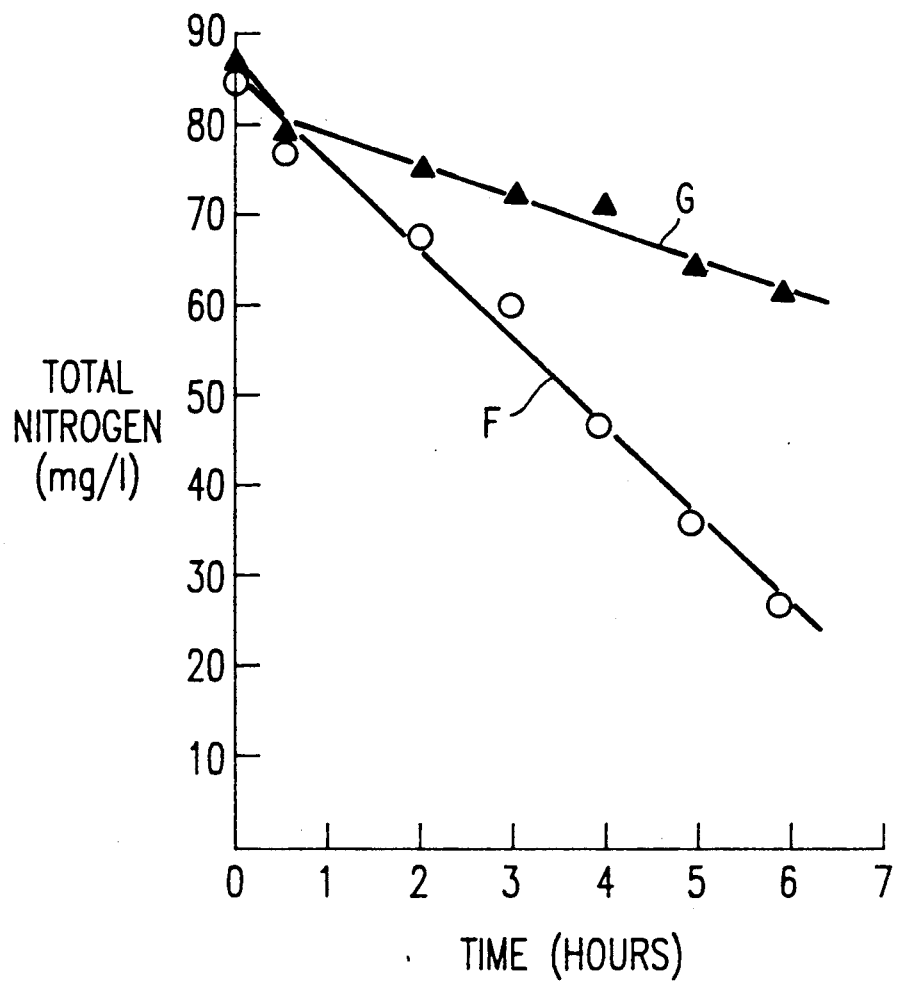
In FIG. 3, line F represents the denitrifying activity of microbial cell immobilized in freeze-thaw PVA gel of the present invention (Example 3).

The result is shown in FIG. 3.

The activity of PVA gel of this invention (line F in FIG. 3) and that of PVA gel obtained by the use of boric acid (line G in FIG. 3) (expressed by the rate of denitrification) were 0.098 mg (total-Nitrogen)/g (gel)/hour and 0.026 mg (total-Nitrogen)/g (gel)/hour, respectively, showing that PVA gel of this invention has about four times higher activity than PVA gel obtained by the use of boric acid. (The rate of denitrification was calculated from the slope of linear portions (0.5 to 3 hours) in the curves of FIG. 3.)

What is claimed is:

1. A process for manufacturing a high-strength, spherical hydrated gel containing a microorganism immobilized therein, which comprises forming spherical gel beads by dropwise addition of an aqueous solution containing (A) a microorganism, (B) about 3 to about 40% by weight polyvinyl alcohol, and (C) about 0.2 to about 4% by weight water-soluble polysaccharide capable of gelation upon contact with a polyvalent metal ion, to an aqueous solution of a compound which produces said polyvalent metal ion in aqueous medium to obtain spherical gel beads; and subjecting the spherical gel beads to at least one cycle of freezing, at a temperature not higher than $-5°$ C., and thawing, thereby causing gelation of said polyvinyl alcohol.

2. The process of claim 1, wherein the cycle of freeze-thawing is repeated at least two times.

3. The process of claim 1, wherein said water-soluble polysaccharide capable of gelation upon contact with a polyvalent metal ion is sodium alginate.

4. The process of claim 1, wherein said compound which produces said polyvalent metal ion in aqueous medium is calcium chloride.

5. A high-strength spherical hydrated gel containing a microorganism immobilized therein, produced by the process comprising the steps:
   (i) adding in a dropwise manner an aqueous solution containing (a) a microorganism, (b) about 3 to about 40% by weight polyvinyl alcohol, and (c) about 0.2 to about 4% by weight water-soluble polysaccharide capable of gelation upon contact with a polyvalent metal ion, to an aqueous solution of a compound which produces said polyvalent metal ion, to obtain spherical gel beads; and
   (ii) subjecting said spherical gel beads to at least one cycle of freezing, at a temperature not higher than $-5°$ C., and thawing, thereby causing gelation of said polyvinyl alcohol.

6. The hydrated gel of claim 5, wherein said cycle of freezing and thawing is repeated at least two times.

7. The hydrated gel of claim 5, wherein said water-soluble polysaccharide is sodium alginate.

8. The hydrated gel of claim 5, wherein said compound which produces a polyvalent metal ion is calcium chloride.

* * * * *